US012805034B2

(12) United States Patent
Hosokawa

(10) Patent No.: US 12,805,034 B2
(45) Date of Patent: Nov. 17, 2026

(54) RADIATION DETECTOR, X-RAY COMPUTER TOMOGRAPHIC APPARATUS, AND MANUFACTURING METHOD

(71) Applicant: CANON KABUSHIKI KAISHA, Tokyo (JP)

(72) Inventor: Hibiki Hosokawa, Nasushiobara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 156 days.

(21) Appl. No.: 18/585,328

(22) Filed: Feb. 23, 2024

(65) Prior Publication Data

US 2024/0304652 A1 Sep. 12, 2024

(30) Foreign Application Priority Data

Mar. 8, 2023 (JP) ................................ 2023-035870

(51) Int. Cl.
*G01T 1/24* (2006.01)
*A61B 6/06* (2006.01)
(Continued)

(52) U.S. Cl.
CPC ........... *H10F 39/1895* (2025.01); *A61B 6/06* (2013.01); *G01T 1/20182* (2020.05); *G01T 1/24* (2013.01);
(Continued)

(58) Field of Classification Search
CPC ..... A61B 6/4266; A61B 6/032; A61B 6/4078; A61B 6/4233; A61B 6/4283;
(Continued)

(56) References Cited

U.S. PATENT DOCUMENTS 7,781,741 B2 8/2010 Narasimhan et al.
9,480,446 B2 11/2016 Hashimoto et al.
(Continued)

FOREIGN PATENT DOCUMENTS

JP 2005-296340 A 10/2005
JP 2007-117733 A 5/2007
(Continued)

*Primary Examiner* — Uzma Alam
*Assistant Examiner* — Fani Polyzos Boosalis
(74) *Attorney, Agent, or Firm* — Oblon, McClelland, Maier & Neustadt, L.L.P.

(57) ABSTRACT

A radiation detector according to embodiments includes a first detector module and a second detector module. The first detector module includes, on a surface facing a radiation generation source, a sensitive portion that outputs an analog signal corresponding to incident radiation and an insensitive portion provided with at least a portion of a transmission path of the analog signal output from the sensitive portion. The second detector module is a detector module different from the first detector module, and includes, on a surface facing the radiation source, a sensitive portion that outputs an analog signal corresponding to the incident radiation and an insensitive portion provided with at least a portion of a transmission path of the analog signal output from the sensitive portion. The sensitive portion of the first detector module and the insensitive portion of the second detector module are arranged so as to overlap each other.

14 Claims, 7 Drawing Sheets

(51) Int. Cl.
*G01T 1/20* (2006.01)
*H10F 39/00* (2025.01)
*H10F 39/18* (2025.01)
*A61B 6/42* (2024.01)

(52) U.S. Cl.
CPC ....... *H10F 39/018* (2025.01); *H10F 39/1898* (2025.01); *A61B 6/4258* (2013.01)

(58) Field of Classification Search
CPC ....... A61B 6/5241; A61B 6/06; A61B 6/4258; G01T 1/20; G01T 1/20182; G01T 1/247; G01T 1/24; H10F 39/1895; H10F 39/018; H10F 39/1898
See application file for complete search history.

(56) References Cited

U.S. PATENT DOCUMENTS

| | | | | |
|---|---|---|---|---|
| 2004/0200971 | A1* | 10/2004 | De Keyser | G01N 23/04<br>378/98.8 |
| 2007/0096029 | A1 | 5/2007 | Narasimhan et al. | |
| 2014/0233690 | A1 | 8/2014 | Hashimoto et al. | |
| 2021/0204889 | A1* | 7/2021 | Jacob | G01T 1/20182 |

FOREIGN PATENT DOCUMENTS

| | | | | | |
|---|---|---|---|---|---|
| JP | 2012-40140 | A | | 3/2012 | |
| JP | 2012040140 | A | * | 3/2012 | A61B 6/00 |
| JP | 2014-62898 | A | | 4/2014 | |
| JP | 2019-48181 | A | | 3/2019 | |
| JP | 2021-148468 | A | | 9/2021 | |
| WO | WO-2021063663 | A1 | * | 4/2021 | G03F 9/7088 |

* cited by examiner

RADIATION DETECTOR, X-RAY COMPUTER TOMOGRAPHIC APPARATUS, AND MANUFACTURING METHOD

CROSS-REFERENCE TO RELATED APPLICATIONS

This application is based upon and claims the benefit of priority from Japanese Patent Application No. 2023-035870, filed on Mar. 8, 2023; the entire contents of which are incorporated herein by reference.

FIELD

Embodiments disclosed herein and in the drawings relate generally to a radiation detector, an X-ray computer tomographic apparatus, and a manufacturing method.

BACKGROUND

In recent years, X-ray computer tomographic (CT) apparatuses have achieved a wider coverage, and methods have been known to configure an X-ray detector by arranging a plurality of small units of detector modules in a channel direction and a row direction from the viewpoint of yield and component commonality.

For example, as a general method, a method is known of using a 4-side tileable detector module that is configured such that a plane of incidence of X-rays is formed in a rectangular shape and all the four sides of the plane of incidence are included in a sensitive portion that detects the X-rays. However, in the 4-side tileable detector module, signals output from a photodiode array need to be read from a back surface (surface opposite the plane of incidence of the X-rays), which causes a problem of high cost.

In contrast, a method is also known of using a 3-side tileable detector module that is configured such that one of the four sides of the plane of incidence is included in an insensitive portion that does not detect the X-rays. The 3-side tileable detector module has a structure that can read the signals from the same side as the plane of incidence of the photodiode array in the insensitive portion, and can be manufactured at a lower cost than that of the 4-side tileable detector module. However, in the case of using the 3-side tileable detector module, although the module can be manufactured at a lower cost, the insensitive portion generates an insensitive area. Therefore, a problem arises that a complementary process is required to compensate for the insensitive area, and, for example, a dummy scintillator is required to protect the insensitive portion from the X-rays as needed.

This problem is not limited to arising in the X-ray detector of the X-ray CT apparatuses, but can also arise in the same manner in a radiation detector of other radiation diagnosis devices, such as a gamma radiation detector of positron emission tomography (PET) devices and single photon emission computed tomography (SPECT) devices.

DETAILED DESCRIPTION

Figure 1:
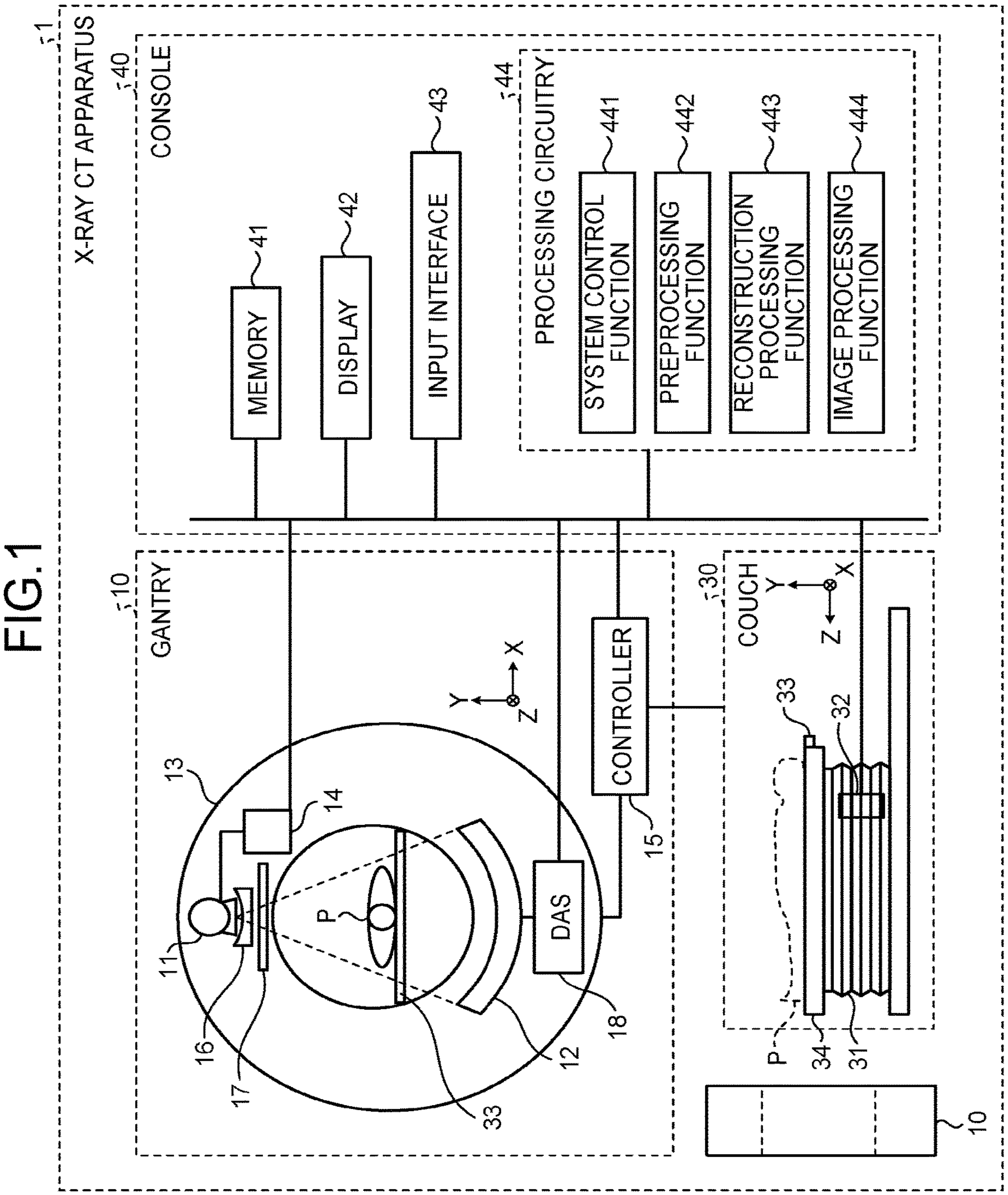
FIG. 1 is a diagram illustrating a configuration example of an X-ray computer tomographic (CT) apparatus according to a first embodiment.

A radiation detector according to embodiments includes a first detector module and a second detector module. The first detector module includes, on a surface facing a radiation generation source, a sensitive portion that outputs an analog signal corresponding to incident radiation and an insensitive portion provided with at least a portion of a transmission path of the analog signal output from the sensitive portion. The second detector module is a detector module different from the first detector module, and includes, on a surface facing the radiation source, a sensitive portion that outputs an analog signal corresponding to the incident radiation and an insensitive portion provided with at least a portion of a transmission path of the analog signal output from the sensitive portion. The sensitive portion of the first detector module and the insensitive portion of the second detector module are arranged so as to overlap each other.

The following describes the embodiments of the radiation detector, an X-ray computer tomographic (CT) apparatus, and a manufacturing method, disclosed herein with reference to the drawings. The configurations illustrated in the drawings are schematic, and dimensions of each component and ratios of the dimensions between the components illustrated in the drawings may differ from those of the actual components. In addition, the dimensions of the same component and the ratios of the dimensions between the components may be illustrated differently between the drawings.

In the following embodiments, a case will be described where the technology disclosed herein is applied to an X-ray detector of an X-ray CT apparatus.

First Embodiment

FIG. 1 is a diagram illustrating a configuration example of the X-ray CT apparatus according to a first embodiment.

For example, as illustrated in FIG. 1, an X-ray CT apparatus 1 according to the present embodiment includes a gantry 10, a couch 30, and a console 40. In the present embodiment, a Z-axis direction is defined as a direction of a rotation axis of a rotary frame 13 or a longitudinal direction of a couchtop 33 of a couch 30 in a non-tilt state; an X-axis direction is defined as an axis direction that is orthogonal to the Z-axis direction and horizontal to the floor surface; and a Y-axis direction is defined as an axis direction that is orthogonal to the Z-axis direction and orthogonal to the floor surface.

The gantry 10 is a device that emits X-rays to a subject P such as a patient, detects the X-rays transmitted through the subject P, and outputs the detected data to the console 40. Specifically, the gantry 10 includes an X-ray tube 11, an X-ray detector 12, the rotary frame 13, an X-ray high-voltage device 14, a controller 15, a wedge 16, an X-ray diaphragm 17, and a data acquisition system (DAS) 18. For convenience of illustration, FIG. 1 illustrates the gantry 10 viewed from the X-axis direction and the gantry 10 viewed from the Z-axis direction. However, in reality, the X-ray CT apparatus 1 include one gantry 10.

The X-ray tube 11 is a vacuum tube including a cathode (filament) that generates thermions and an anode (target) that receives impact of the thermions to generate the X-rays. An application of a high voltage from the X-ray high-voltage device 14 causes the X-ray tube 11 to emit the thermions from the cathode toward the anode so as to generate the X-rays emitted to the subject P. For example, the X-ray tube 11 is a rotating anode X-ray tube that generates the X-rays by emitting the thermions to the anode that is rotating.

The wedge 16 is a filter to regulate the amount of the X-rays emitted from the X-ray tube 11. Specifically, the wedge 16 is a filter that transmits and attenuates the X-rays emitted from the X-ray tube 11 so that the X-rays emitted from the X-ray tube 11 to the subject P have a predetermined distribution. For example, the wedge 16 is a filter made by processing aluminum so as to have a predetermined target angle and a predetermined thickness. The wedge 16 is also called a wedge filter or a bow-tie filter.

The X-ray diaphragm 17 includes a lead plate or the like to narrow an irradiated range of the X-rays having passed through the wedge 16, and has a slit formed by combining a plurality of the lead plates or the like. The X-ray diaphragm 17 may also be called a collimator.

The X-ray detector 12 detects the X-rays that have been emitted from the X-ray tube 11 and passed through the subject P. Specifically, the X-ray detector 12 has a structure in which a plurality of X-ray detection element columns are included, each having a plurality of X-ray detection elements arranged in a channel direction along one circular arc centered on the focal point of the X-ray tube 11, and the X-ray detection element columns are arranged in a row direction (slice direction) orthogonal to the channel direction.

In the present embodiment, the X-ray detector 12 is an indirect conversion detector that includes a scintillator and a photodiode array. The scintillator converts the X-rays incident thereon into light. The photodiode array is optically connected to the scintillator, and has an array of a plurality of photodiodes that convert the light converted by the scintillator into analog signals. The scintillator includes a plurality of scintillator elements arranged so as to individually correspond to the respective photodiodes included in the photodiode array. In this case, a corresponding pair of one of the scintillator elements and one of the photodiodes is an example of each of the X-ray detection elements.

The X-ray detector 12 includes an analog-to-digital converter (ADC) to convert an analog signal output from each of the X-ray detection elements into a digital signal, and uses the ADC to generate detector data. The X-ray detector 12 outputs the generated detector data to the DAS 18. For example, in order to reduce scattered X-rays, a collimator may be provided on the X-ray incident plane side of the X-ray detector 12. This collimator may be called a scattered ray removal grid or a post-collimator.

The DAS 18 collects the detected data output from the X-ray detector 12. The DAS 18 transfers the collected detected data to the console 40.

The X-ray high-voltage device 14 includes a high voltage generation device that includes electrical circuitry such as a transformer and a rectifier and has a function to generate a high voltage to be applied to the X-ray tube 11, and an X-ray control device that controls an output voltage corresponding to the X-ray output emitted by the X-ray tube 11. The high voltage generation device may be a transformer system or an inverter system. The X-ray high-voltage device 14 may be provided on the rotary frame 13 (to be described later) or on a fixed frame (not illustrated) side of the gantry 10. The fixed frame is a support frame that rotatably supports the rotary frame 13.

The rotary frame 13 is a circular ring frame with the X-ray tube 11 and the X-ray detector 12 fixed thereto, and rotates about the rotation axis. Specifically, the rotary frame 13 supports the X-ray tube 11 and the X-ray detector 12 in a state of facing each other with the rotation axis interposed therebetween, and is controlled by the controller 15 (to be described later) to rotate the X-ray tube 11 and the X-ray detector 12. The rotary frame 13 further includes and supports the X-ray high-voltage device 14 in addition to the X-ray tube 11 and the X-ray detector 12.

The rotary frame 13 is rotatably supported by a non-rotating portion (for example, the fixed frame, which is not illustrated in FIG. 1) of the gantry 10. A rotating mechanism includes, for example, a motor that generates a rotary drive force and a bearing that transmits the rotary drive force to the rotary frame 13 to rotate it. The motor is provided, for example, at the non-rotating portion, and the bearing is physically connected to the rotary frame 13 and the motor. The rotary frame 13 rotates according to torque of the motor.

The rotary frame 13 and the non-rotating portion are each provided with a non-contact or contact type communication circuit, which allows communication of a unit supported by the rotary frame 13 with an external device at the non-rotating portion or the gantry 10. For example, when optical communication is employed as a non-contact communication method, the detected data generated by the DAS 18 is transmitted from a transmitter having a light-emitting diode (LED) provided on the rotary frame 13 to a receiver having a photodiode provided at the non-rotating portion of the gantry 10 through the optical communication, and further forwarded from the non-rotating portion to the console 40 by a transmitter. As a communication method other than the method described above, non-contact data transmission methods, such as a capacitive coupling method and a radio wave method, and contact-type data transmission methods using slip rings and electrode brushes can be employed.

The controller 15 includes processing circuitry having a central processing unit (CPU) or the like, and a drive mechanism such as a motor and an actuator. The controller 15 has a function to control operations of the gantry 10 and the couch 30 by receiving input signals from an input interface 43 mounted on the console 40 or the gantry 10. For example, by receiving the input signals, the controller 15 performs control to rotate the rotary frame 13, control to tilt of the gantry 10, and control to operate the couch 30 and the couchtop 33. The control to tilt the gantry 10 is performed by the controller 15 by rotating the rotary frame 13 about an axis parallel to the X-axis direction based on tilt angle information received through the input interface 43 mounted on the gantry 10. The controller 15 may be provided on the gantry 10 or the console 40.

The couch 30 is a device to place and move the subject P to be scanned, and includes a base 31, a couch drive device 32, the couchtop 33, and a support frame 34. The base 31 is a chassis that supports the support frame 34 in a vertically movable manner. The couch drive device 32 is a motor or an actuator that moves the couchtop 33 on which the subject P is placed in the long axis direction of the couchtop 33. The couchtop 33 provided on the upper surface of the support frame 34 is a plate on which the subject P is placed. The couch drive device 32 may move the support frame 34, in addition to the couchtop 33, in the long axis direction of the couchtop 33.

The console 40 is a device that receives operations of the X-ray CT apparatus 1 by an operator, and reconstructs CT image data using the detected data collected by the gantry 10. The console 40 includes a memory 41, a display 42, the input interface 43, and processing circuitry 44. Although an example in which the console 40 and the gantry 10 are separate devices is described herein, the gantry 10 may include the console 40 or some of the components of the console 40.

The memory 41 is implemented by, for example, semiconductor memory devices such as a random-access memory (RAM) and a flash memory, a hard disk, and an optical disc. The memory 41 stores therein, for example, projection data and the CT image data.

The display 42 displays thereon various types of information. The display 42 outputs, for example, medical images (CT images) generated by the processing circuitry 44 and a graphical user interface (GUI) for receiving various operations from the operator. The display 42 is, for example, a liquid crystal display or a cathode-ray tube (CRT) display. The display 42 may be provided, for example, on the gantry 10. For example, the display 42 may be a desktop type, or may be configured as a tablet computer or the like capable of wireless communication with the main unit of the console 40.

The input interface 43 receives various input operations from the operator, converts the received input operations into electrical signals, and outputs the electrical signals to the processing circuitry 44. For example, the input interface 43 receives, from the operator, scan conditions when collecting the projection data, reconstruction conditions when reconstructing the CT image data, image processing conditions when generating post-processed image data from the CT image data, and the like. The input interface 43 can be implemented by, for example, a mouse, a keyboard, a trackball, switches, buttons, and a joystick. The input interface 43 may be provided, for example, on the gantry 10. For example, the input interface 43 may be configured as a tablet computer or the like capable of wireless communication with the main unit of the console 40.

The processing circuitry 44 controls the operations of the entire X-ray CT apparatus 1. For example, the processing circuitry 44 performs a system control function 441, a preprocessing function 442, a reconstruction processing function 443, and an image processing function 444.

The system control function 441 controls various functions of the processing circuitry 44 based on the input operations received from the operator through the input interface 43. For example, the system control function 441 controls CT scans performed in the X-ray CT apparatus 1. The system control function 441 also controls the generation and display of the CT image data in the console 40 by controlling the preprocessing function 442, the reconstruction processing function 443 and the image processing function 444.

The preprocessing function 442 generates the projection data by performing preprocessing, such as logarithmic transformation processing, offset correction processing, sensitivity correction processing between channels, and beam hardening correction, on the detected data output from the DAS 18. The data before the preprocessing (detected data) and the data after the preprocessing may be collectively referred to as the projection data.

The reconstruction processing function 443 generates the CT image data (reconstructed image data) by performing reconstruction processing using, for example, a filter-corrected back projection method or a successive approximation reconstruction method on the projection data generated by the preprocessing function 442.

The image processing function 444 converts the CT image data generated by the reconstruction processing function 443 into tomographic image data or three-dimensional image data of an arbitrary section using a known method, based on the input operations received from the operator through the input interface 43. The reconstruction processing function 443 may directly generate the three-dimensional image data.

The processing circuitry 44 is implemented by, for example, a processor. In that case, the respective processing functions of the processing circuitry 44 are stored in the memory 41 in the form of computer programs executable by a computer. The processing circuitry 44 reads each of the computer programs from the memory 41 and executes it to perform the function corresponding to the computer program. In other words, the processing circuitry 44 that has read each of the computer programs has a corresponding one of the processing functions illustrated in the processing circuitry 44 in FIG. 1.

The description has been made that the single processing circuitry 44 performs each of the processing functions described above. However, for example, the processing circuitry 44 may be configured by combining a plurality of independent processors, and each of the processors may execute a computer program to perform each of the processing functions. The respective processing functions included in the processing circuitry 44 may be performed by being distributed or integrated into a single processing circuit or multiple processing circuits as appropriate. The respective processing functions included in the processing circuitry 44 may be performed by a mixture of hardware such as circuitry and software. Although the example has been described in which the single memory 41 stores therein the computer programs corresponding to the respective processing functions, embodiments are not limited to this example. For example, a configuration may be employed in which a plurality of storage circuits are arranged in a distributed manner, and the processing circuitry 44 reads corresponding computer programs from individual storage circuits and executes the read computer programs.

The overall configuration of the X-ray CT apparatus 1 according to the present embodiment has been described above.

In recent years, the X-ray CT apparatuses have achieved a wider coverage, and methods have been known to configure the X-ray detector by arranging a plurality of small units of the detector modules in the channel direction and the row direction from the viewpoint of yield and component commonality.

For example, as a general method, a method is known of using a 4-side tileable detector module that is configured such that the plane of incidence of the X-rays is formed in a rectangular shape and all the four sides of the plane of incidence are included in the sensitive portion that detects the X-rays. However, in the 4-side tileable detector module, the signals output from the photodiode array need to be read from a back surface (surface opposite the plane of incidence of the X-rays), which causes a problem of high cost.

In contrast, a method is also known of using a 3-side tileable detector module that is configured such that one of the four sides of the plane of incidence is included in an insensitive portion that does not detect the X-rays. The 3-side tileable detector module has a structure that can read the signals from the same side as the plane of incidence of the photodiode array in the insensitive portion, and can be manufactured at a lower cost than that of the 4-side tileable detector module. However, in the case of using the 3-side tileable detector module, although the module can be manufactured at a lower cost, the insensitive portion generates an insensitive area. Therefore, a problem arises that a complementary process is required to compensate for the insensitive area, and, for example, a dummy scintillator is required to protect the insensitive portion from the X-rays as needed.

For this reason, in the present embodiment, when configuring the X-ray detector 12 by arranging the 3-side tileable detector modules, the insensitive area generated by the insensitive portion included in the detector module can be reduced. The following describes a configuration of the X-ray detector 12 according to the present embodiment in detail.

Figure 2:
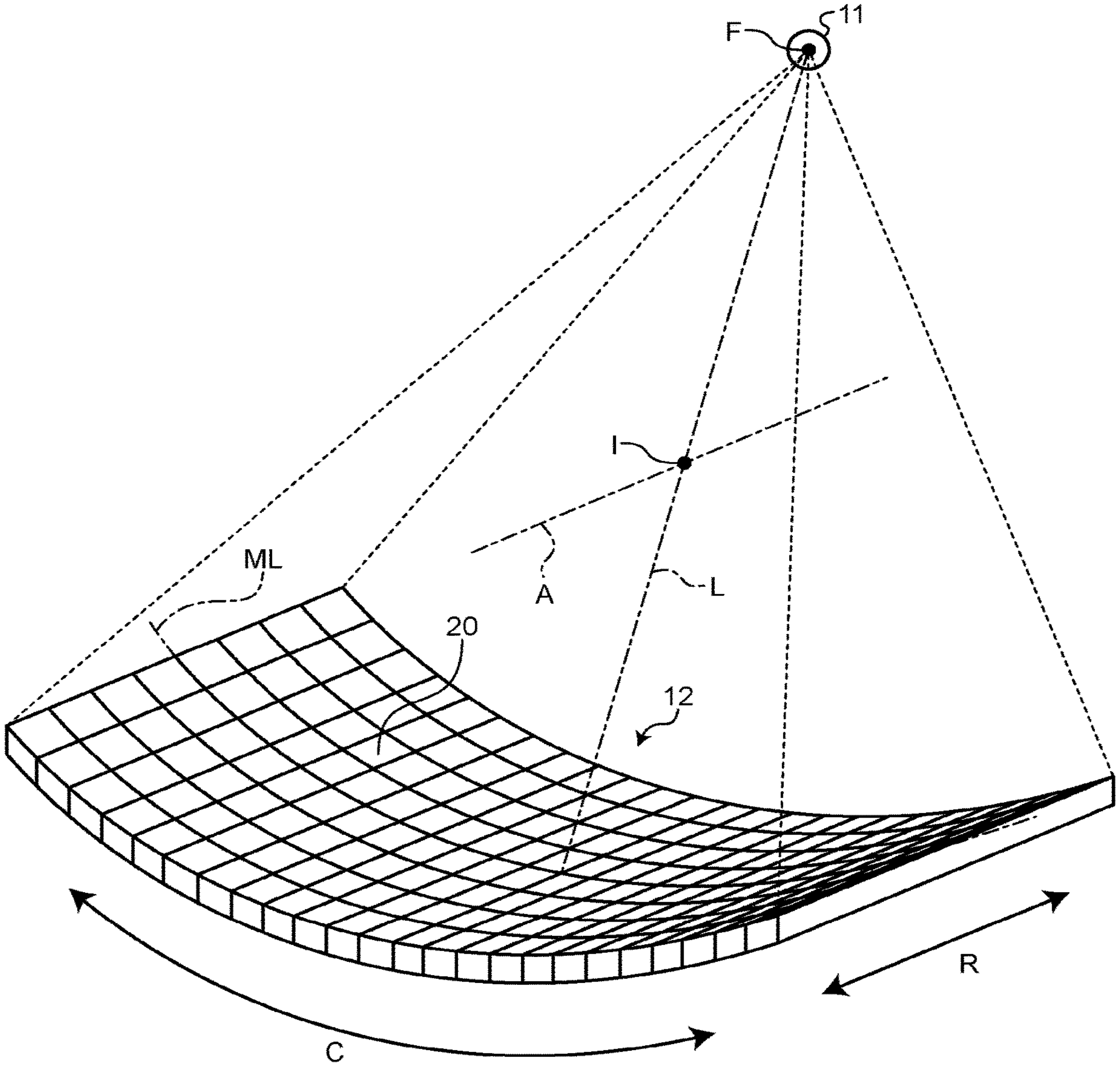
FIG. 2 is a view illustrating a configuration example of an X-ray detector according to the first embodiment.

FIG. 2 is a view illustrating a configuration example of the X-ray detector 12 according to the first embodiment.

As illustrated in, for example, FIG. 2, the X-ray detector 12 is configured by arranging a plurality of detector modules 20 along each of a channel direction C along one circular arc centered on a focal point F of the X-ray tube 11 and a row direction R orthogonal to the channel direction C. Hereinafter, one row of the detector modules 20 arranged along the row direction R is referred to as "row direction detector module group". The rotation of the rotary frame 13 described above rotates the X-ray tube 11 and the X-ray detector 12 about a rotation axis A parallel to the row direction R passing through an isocenter I with the axis interposed between the X-ray tube 11 and the X-ray detector 12. A straight line L illustrated in FIG. 2 indicates a straight line that passes through the focal point F and the isocenter I of the X-ray tube 11 and intersects the X-ray detector 12. A straight line ML illustrated in FIG. 2 indicates a line along the channel direction C (hereafter referred to as "row-directional center line") that passes through a point where the straight line L intersects the X-ray detector 12.

Each of the detector modules 20 is the 3-side tileable detector module, and the detector modules 20 have the same structure. Specifically, each of the detector modules 20 has, on a surface facing the X-ray tube 11, the sensitive portion that outputs an analog signal corresponding to incident X-rays and the insensitive portion provided with at least a portion of the transmission path of the analog signal output from the sensitive portion.

Figure 3:
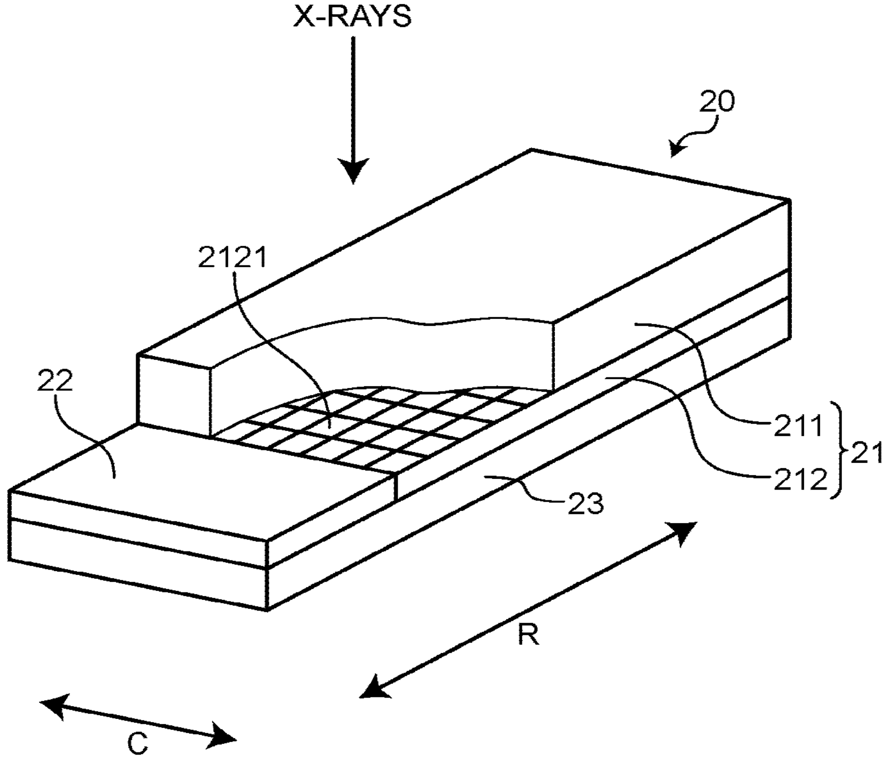
FIG. 3 is a view illustrating a configuration example of a detector module according to the first embodiment.

FIG. 3 is a view illustrating a configuration example of the detector module 20 according to the first embodiment.

As illustrated in, for example, FIG. 3, the detector module 20 includes a sensitive portion 21, an insensitive portion 22, and a substrate 23. The sensitive portions 21 and the insensitive portions 22 are mounted so as to be arranged adjacent to one another in the row direction R on a surface of the substrate 23 facing the X-ray tube 11.

The sensitive portion 21 includes a scintillator 211 and a photodiode array 212. The scintillator 211 converts the incident X-rays into light. The photodiode array 212 is optically connected to the scintillator 211, and includes an array of a plurality of photodiodes 2121 that convert the light converted by the scintillator 211 into analog signals. The scintillator 211 includes a plurality of scintillator elements arranged so as to individually correspond to the respective photodiodes 2121 included in the photodiode array 212.

The insensitive portion 22 includes the ADC that converts the analog signals output from the sensitive portion 21 into digital signals. The ADC is an example of an analog-to-digital converter.

In the configuration described above, in the present embodiment, the X-ray detector 12 can reduce the insensitive area generated by the insensitive portion 22 included in the detector module 20.

Specifically, in the present embodiment, in the X-ray detector 12, the detector modules 20 arranged in the row direction R are arranged such that, for each pair of the adjacent detector modules 20, the sensitive portion 21 of one of the detector modules 20 overlaps the insensitive portion 22 of the other of the detector modules 20.

Figure 4:
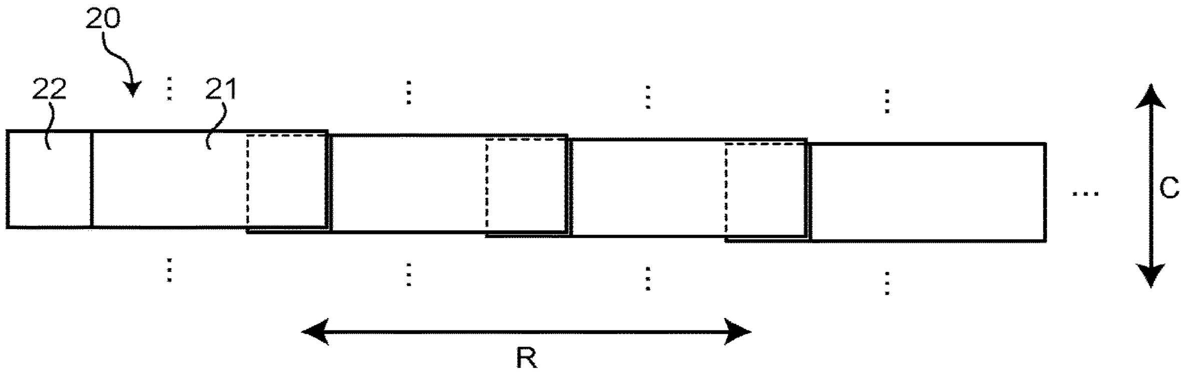
FIG. 4 is a view illustrating an arrangement example of the detector modules according to the first embodiment.
Figure 5:
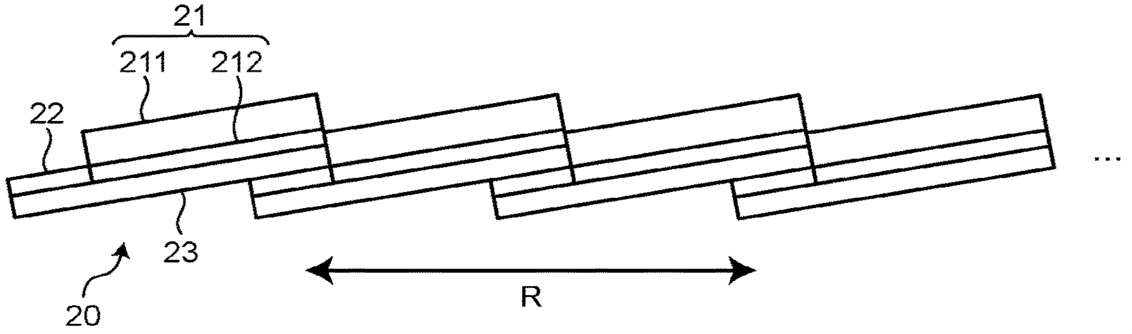
FIG. 5 is another view illustrating the arrangement example of the detector modules according to the first embodiment.

FIGS. 4 and 5 are views illustrating an arrangement example of the detector modules 20 according to the first embodiment.

FIGS. 4 and 5 illustrate the detector modules 20 included in one row direction detector module group included in the X-ray detector 12. FIG. 4 illustrates a state of viewing the row direction detector module group from a direction of incidence of the X-rays, and FIG. 5 illustrates a state of viewing the row direction detector module group from the channel direction C.

As illustrated in, for example, FIGS. 4 and 5, in the present embodiment, the detector modules 20 are arranged in one row in the same direction along the row direction R so as to form one row direction detector module group.

In the present embodiment, the detector modules 20 arranged in the row direction R are arranged at the same tilt angle with respect to the row direction R so that the respective planes of incidence of the X-rays face in the same direction. That is, the detector modules 20 arranged in the row direction R are arranged such that each of the detector modules 20 is tilted at a constant angle with respect to the row direction R.

In the present embodiment, in the detector modules 20 arranged in the row direction R, the sensitive portion 21 of each of the detector modules 20 is arranged so as to overlap the top of the insensitive portion 22 of the adjacent detector module 20.

According to the configuration described above, in the detector modules 20 arranged in the row direction R, the sensitive portion 21 of one of the adjacent detector modules 20 overlaps the insensitive portion 22 of the other thereof. Thereby, the insensitive area generated by the insensitive portion 22 included in the detector module 20 can be reduced. This feature can eliminate the need for the complementary process for compensating for the insensitive area. In addition, the mounting space for the X-ray detector 12 can be reduced.

Furthermore, according to the configuration described above, in the detector modules 20 arranged in the row direction R, the sensitive portion 21 of one of the adjacent detector modules 20 overlaps the top of the insensitive portion 22 of the other thereof. Thereby, the insensitive portion 22 can be shielded from the X-rays incident thereon by the sensitive portion 21. This feature can eliminate the need for the dummy scintillator or the like to protect the insensitive portion 22 from the X-rays, and thus can reduce the cost of mounting the X-ray detector 12.

While the first embodiment has been described above, the first embodiment described above can also be implemented by changing the configuration of the X-ray detector 12 as appropriate. Therefore, the following describes various modifications of the first embodiment as other embodiments. In the following embodiments, mainly differences from the first embodiment will be described, and the description overlapping that of the first embodiment will not be made in detail.

Second Embodiment

For example, in the first embodiment described above, the exemplary case has been described where the detector modules 20 arranged in the row direction R are arranged such that the respective planes of incidence of the X-rays face in the same direction. However, the embodiments are not limited to this case. For example, the plane of incidence of the X-rays of each of the detector modules 20 may face the focal point of the X-ray tube 11. In the following description, such an example is described as a second embodiment.

Figure 6:
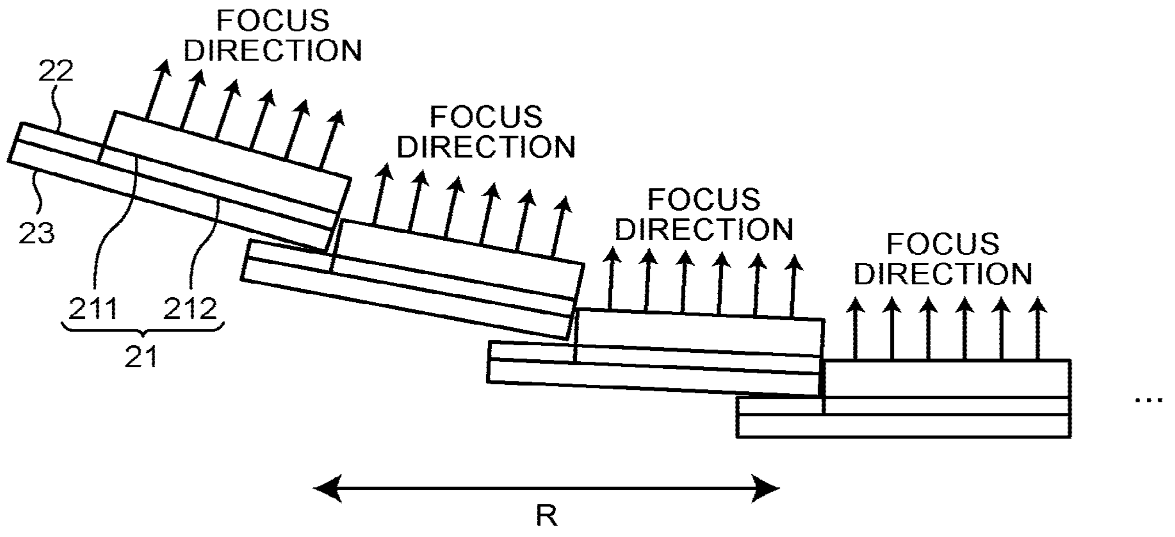
FIG. 6 is a view illustrating an arrangement example of the detector modules according to a second embodiment.

FIG. 6 is a view illustrating an arrangement example of the detector modules 20 according to the second embodiment.

FIG. 6 illustrates the detector modules 20 included in one of two ranges obtained by dividing one row direction detector module group included in the X-ray detector 12 into the two ranges by the row-directional center line ML (refer to FIG. 2), and illustrates a state of viewing the row direction detector module group from the channel direction C.

For example, as illustrated in FIG. 6, in the present embodiment, the detector modules 20 arranged in the row direction R are arranged individually at different tilt angles with respect to the row direction R so that the respective planes of incidence of the X-rays face the focal point of the X-ray tube 11. That is, the detector modules 20 arranged in the row direction R are arranged so as to be more largely tilted with respect to the row direction R as the detector module 20 is farther from the row-directional center line ML.

In the present embodiment, in the detector modules 20 arranged in the row direction R, the sensitive portion 21 of each of the detector modules 20 is arranged so as to overlap the top of the insensitive portion 22 of the adjacent detector module 20.

According to the configuration described above, the detector modules 20 arranged in the row direction R are arranged such that the plane of incidence of each of the detector modules 20 faces the focal point of the X-ray tube 11. Thereby, oblique incidence of the X-rays in a cone angle direction with respect to the detector module 20 can be restrained. The cone angle herein is an angle that represents the amount of spread of the X-rays emitted from the X-ray tube 11 along the row direction R. This feature can improve the imaging quality of the CT image. In addition, the detector modules 20 can be arranged in a circular arc shape both in the channel direction C and in the row direction R, allowing the X-ray detector 12 to be configured as a spherical detector.

Third Embodiment

For example, in the first embodiment described above, in the detector modules 20 arranged in the row direction R, the sensitive portion 21 of one of the adjacent detector modules 20 overlaps the top of the insensitive portion 22 of the other thereof. However, the embodiments are not limited to this arrangement. For example, a two-dimensional collimator may be used to block the X-rays incident on a side surface of the sensitive portion 21 of the detector module 20 that is exposed by being superimposed on top of the insensitive portion 22. The following describes such an example as a third embodiment.

Figure 7:
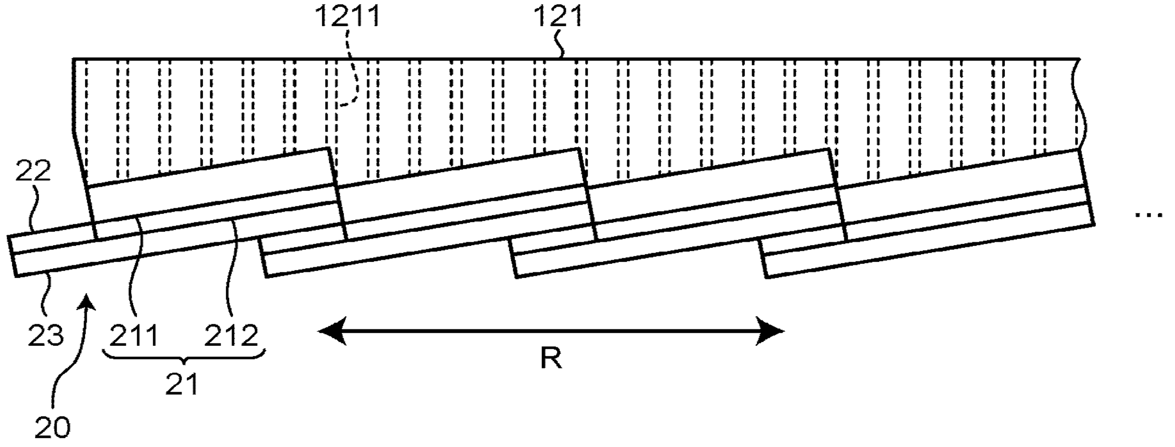
FIG. 7 is a view illustrating an arrangement example of the detector modules according to a third embodiment.

FIG. 7 is a view illustrating an arrangement example of the detector modules 20 according to the third embodiment.

In the same manner as FIG. 5, FIG. 7 illustrates the detector modules 20 included in one row direction detector module group included in the X-ray detector 12, and illustrates a state of viewing the row direction detector module group from the channel direction C.

For example, as illustrated in FIG. 7, in the present embodiment, the X-ray detector 12 further includes a collimator 121 disposed along the planes of incidence of the X-rays of the respective detector modules 20 arranged in the row direction R.

In the present embodiment, the collimator 121 is a two-dimensional collimator disposed over the entire planes of incidence of the X-rays in the X-ray detector 12, and includes a plurality of first shielding plates (illustrated with dashed lines in FIG. 7) parallelly arranged with gaps interposed therebetween in the row direction R and a plurality of second shielding plates parallelly arranged with gaps interposed therebetween in the channel direction C orthogonal to the row direction R.

In addition, in the present embodiment, the first shielding plates included in the collimator 121 include, for each pair of the adjacent detector modules 20, a shielding plate 1211 that blocks scattered X-rays incident on a side surface of the sensitive portion 21 of one of the detector modules 20 at a place where the sensitive portion 21 of the one of the detector modules 20 overlaps the insensitive portion 22 of the other of the detector modules 20.

FIG. 7 illustrates the exemplary case where the first shielding plates included in the collimator 121 are provided at the same angle substantially orthogonal to the row direction R. However, for example, the first shielding plates may be individually provided at different angles with respect to the row direction R so as to each extend along the focus direction of the X-ray tube 11.

According to the configuration described above, the shielding plate 1211 included in the collimator 121 blocks the scattered X-rays incident on the side surface of the sensitive portion 21 of the detector module 20, thereby being capable of increasing the detection accuracy of the X-rays and improving the imaging quality of the CT image.

Fourth Embodiment

For example, in the third embodiment described above, the exemplary case has been described where the X-ray detector 12 further included the collimator 121 disposed along the planes of incidence of the X-rays of the respective detector modules 20 arranged in the row direction R. However, the embodiments are not limited to this case. For example, a two-dimensional collimator integrated with the detector module 20 may be used to block the X-rays incident on the side surface of the sensitive portion 21 of the detector module 20. The following describes such an example as a fourth embodiment.

Figure 8:
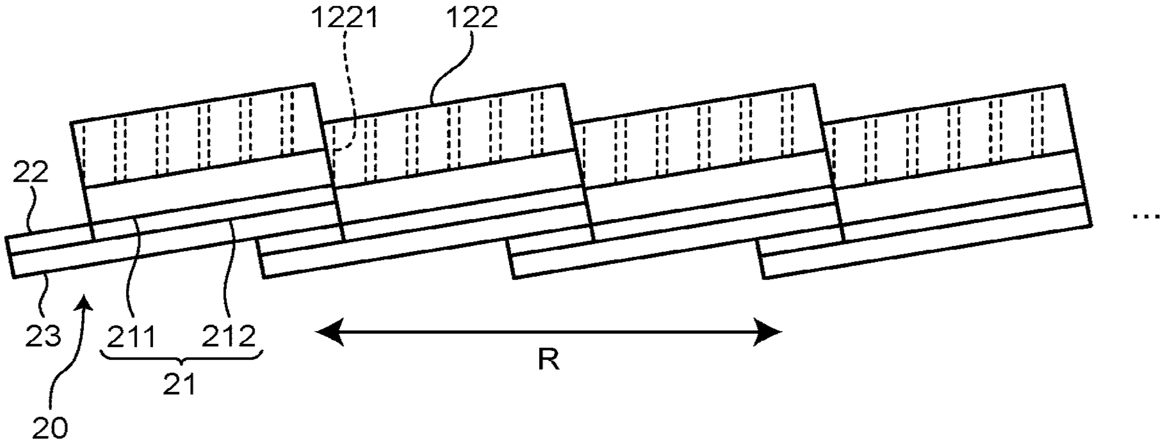
FIG. 8 is a view illustrating an arrangement example of the detector modules according to a fourth embodiment.

FIG. 8 is a view illustrating an arrangement example of the detector modules 20 according to the fourth embodiment.

In the same manner as FIG. 5, FIG. 8 illustrates the detector modules 20 included in the one row direction detector module group included in the X-ray detector 12, and illustrates a state of viewing the row direction detector module group from the channel direction C.

As illustrated in, for example, FIG. 8, in the present embodiment, each of the detector modules 20 included in the X-ray detector 12 individually further includes a collimator 122 disposed on the plane of incidence of the X-rays. The collimator 122 is mounted on the X-ray incident plane side of the scintillator 211 at the sensitive portion 21 so as to be integrated with the detector module 20.

In the present embodiment, each of the collimators 122 includes the first shielding plates (illustrated with dashed lines in FIG. 7) parallelly arranged with gaps interposed therebetween in the row direction R and the second shielding plates parallelly arranged with gaps interposed therebetween in the channel direction C orthogonal to the row direction R.

In the present embodiment, the first shielding plates included in each of the collimators 122 include, for each pair of the adjacent detector modules 20, a shielding plate 1221 that blocks the scattered X-rays incident on a side surface of the sensitive portion 21 of one of the detector modules 20 at a place where the sensitive portion 21 of the one of the detector modules 20 overlaps the insensitive portion 22 of the other of the detector modules 20.

FIG. 8 illustrates the exemplary case where the first shielding plates included in the collimator 122 are provided at the same angle substantially orthogonal to the row direction R. However, for example, the first shielding plates may be individually provided at different angles with respect to the row direction R so as to each extend along the focus direction of the X-ray tube 11.

According to the configuration described above, the shielding plate 1221 included in the collimator 122 blocks the scattered X-rays incident on the side surface of the sensitive portion 21 of the detector module 20, thereby being capable of increasing the detection accuracy of the X-rays and improving the imaging quality of the CT image, in the same manner as in the third embodiment.

Fifth Embodiment

For example, in the third and the fourth embodiments described above, the exemplary cases have been described where the two-dimensional collimator is used to block the X-rays incident on the side surface of the sensitive portion 21 of the detector module 20. However, the embodiments are not limited to these cases. For example, a one-dimensional collimator and a shielding plate that is provided on each of the detector modules 20 may be used to shield the X-rays incident on the side surface of the sensitive portion 21 of the detector module 20. The following describes such an example as a fifth embodiment.

Figure 9:
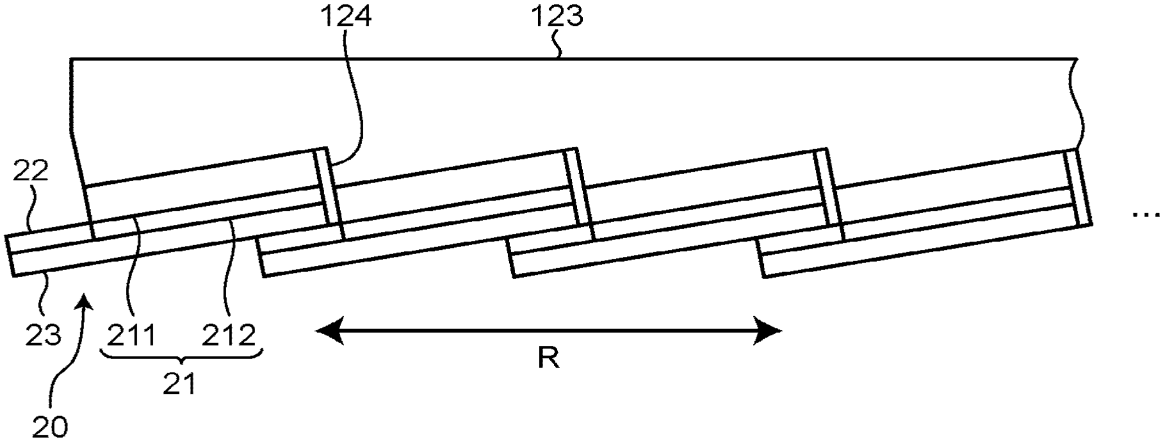
FIG. 9 is a view illustrating an arrangement example of the detector modules according to a fifth embodiment.

FIG. 9 is a view illustrating an arrangement example of the detector modules 20 according to the fifth embodiment.

In the same manner as FIG. 5, FIG. 9 illustrates the detector modules 20 included in the one row direction detector module group included in the X-ray detector 12, and illustrates a state of viewing the row direction detector module group from the channel direction C.

For example, as illustrated in FIG. 9, in the present embodiment, the X-ray detector 12 further includes a collimator 123 disposed along the planes of incidence of the X-rays of the respective detector modules 20 arranged in the row direction R.

In the present embodiment, the collimator 123 is a one-dimensional collimator disposed over the entire planes of incidence of the X-rays in the X-ray detector 12, and includes a plurality of shielding plates parallelly arranged with gaps interposed therebetween in the channel direction C orthogonal to the row direction R.

In the present embodiment, each of the detector modules 20 further includes, on a side surface of the module, a shielding plate 124 that blocks the scattered X-rays incident on the side surface of the sensitive portion 21 of the detector module 20 at a place where the sensitive portion 21 of the detector module 20 overlaps the insensitive portion 22 of the adjacent detector module 20.

According to the configuration described above, the shielding plate 124 provided on the side surface of the sensitive portion 21 of the detector module 20 blocks the scattered X-rays incident on the side surface of the sensitive portion 21 of the detector module 20, thereby being capable of increasing the detection accuracy of the X-rays and improving the imaging quality of the CT image, in the same manner as in the third and the fourth embodiments.

Sixth Embodiment

For example, in the first embodiment described above, the scintillator 211 included in the sensitive portion 21 of the detector module 20 includes the scintillator elements. However, the embodiments are not limited to this example. For example, the scintillator 211 may include reflective materials between the respective scintillator elements. The following describes such an example as a sixth embodiment.

Figure 10:
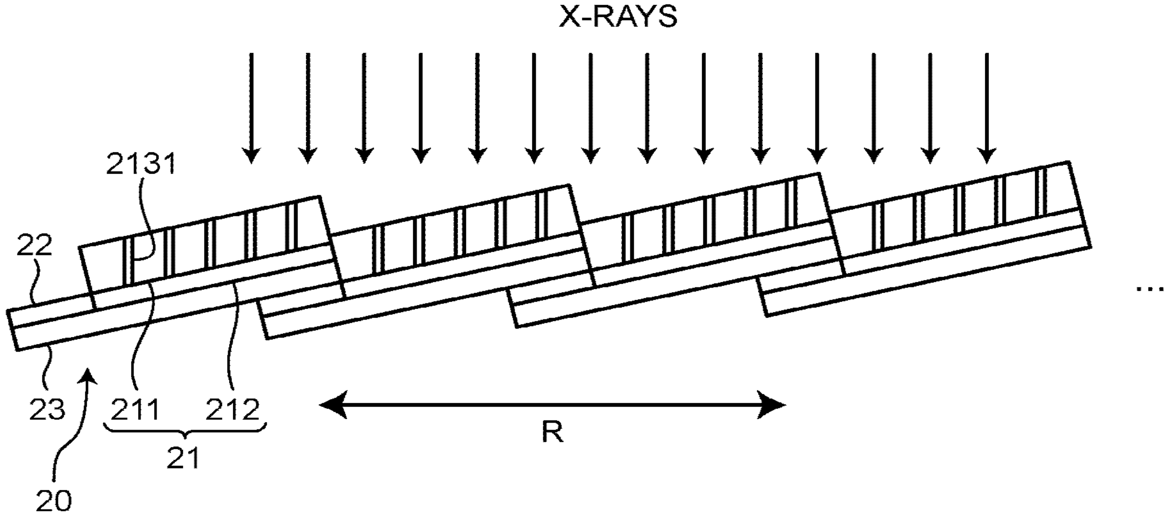
FIG. 10 is a view illustrating an arrangement example of the detector modules according to a sixth embodiment.

FIG. 10 is a view illustrating an arrangement example of the detector modules 20 according to the sixth embodiment.

In the same manner as FIG. 5, FIG. 10 illustrates the detector modules 20 included in one row direction detector module group included in the X-ray detector 12, and illustrates a state of viewing the row direction detector module group from the channel direction C.

For example, as illustrated in FIG. 10, in the present embodiment, the scintillator 211 included in the sensitive portion 21 of each of the detector modules 20 includes a plurality of scintillator elements arranged so as to individually correspond to the respective photodiodes included in the photodiode array 212, and the scintillator elements are separated from one another by reflective materials 2131 tilted along the direction of incidence of the X-rays.

FIG. 10 illustrates the exemplary case where the reflective materials 2131 provided on the scintillator 211 are provided at the same angle substantially orthogonal to the row direction R. However, for example, the reflective materials 2131 may be individually provided at different angles with respect to the row direction R so as to each extend along the focus direction of the X-ray tube 11.

According to the configuration described above, the reflective materials 2131 provided between the scintillator elements included in the scintillator 211 can restrain the oblique incidence of the X-rays with respect to the photodiodes included in the photodiode array 212, thus being capable of improving the X-ray detection accuracy of each of the photodiodes. This feature can improve the resolution of the CT image.

Seventh Embodiment

In the embodiments described above, FIGS. 4 to 10 illustrate the detector modules 20 included in one row direction detector module group included in the X-ray detector 12. When the row direction detector module group is divided into two ranges by the row-directional center line ML (refer to FIG. 2), the detector modules 20 included in one of the ranges and the detector modules 20 included in the other of the ranges may be arranged along the row direction R in the same direction as each other or in directions opposite to each other.

For example, if the detector modules 20 included in the other of the ranges are arranged in the opposite direction, the detector modules 20 included in the other of the ranges are arranged to be arranged in the same row as that of the detector modules 20 included in the one of the ranges in the opposite direction to the detector modules 20 included in the one of the ranges along the row direction R, so as to form one row direction detector module group together with the detector modules 20 included in the one of the ranges. The sensitive portion 21 of the detector module 20 included in the one of the ranges and the sensitive portion 21 of the detector module 20 included in the other of the ranges are arranged so as to be adjacent to each other at the row-directional center line ML.

Eighth Embodiment

In the embodiments described above, the exemplary cases have been described where the X-ray detector 12 is an indirect conversion detector that includes a scintillator and a photodiode array. However, the embodiments are not limited to this case. For example, the X-ray detector 12 may be a direct conversion detector, such as a photon-counting detector.

In that case, the sensitive portion 21 of the detector module 20 includes a semiconductor crystal that outputs an analog signal corresponding to energy contained in the incident X-rays. In the same manner as in the embodiments described above, in the detector modules 20 arranged in the row direction R, the sensitive portion 21 of each of the detector modules 20 is arranged so as to overlap the top of the insensitive portion 22 of the adjacent detector module 20.

In the configuration described above, in the same manner as in the embodiments described above, in the detector modules 20 arranged in the row direction R, the sensitive portion 21 of one of the adjacent detector modules 20 overlaps the top of the insensitive portion 22 of the other thereof. Thereby, the insensitive portion 22 can be shielded from the X-rays incident thereon by the sensitive portion 21. This feature can eliminate the need for the dummy scintillator or the like to protect the insensitive portion 22 from the X-rays, and thus can reduce the cost of mounting the X-ray detector 12.

Ninth Embodiment

In the third to the fifth embodiments described above, FIGS. 7 to 9 illustrate the exemplary cases where the collimator 121, the collimator 122, and the combination of the collimator 123 and the shielding plate 124 are applied to the configuration of the X-ray detector 12 described in the first embodiment. However, the embodiments are not limited to these cases. For example, any one of the collimator 121, the collimator 122, and the combination of the collimator 123 and the shielding plate 124 described in the third to the fifth embodiments may be applied to the configuration of the X-ray detector 12 described in the second embodiment or the configuration of the X-ray detector 12 described in the sixth embodiment.

Tenth Embodiment

In the embodiments described above, the insensitive portion 22 includes the ADC that converts the analog signals output from the sensitive portion 21 into the digital signals. However, the embodiments are not limited to this configuration. For example, the insensitive portion 22 may include various electrical circuits together with or instead of the ADC. For example, the insensitive portion 22 may include wires of wire bonding for reading the analog signals output from the sensitive portion 21 and conductor wires and the like that transmit the analog signals read through the wires of wire bonding to an ADC external to the detector module 20.

Eleventh Embodiment

In the embodiments described above, FIGS. 4 to 10 illustrate the exemplary cases where the sensitive portion 21 of the detector module 20 overlaps substantially the entire surface of the insensitive portion 22 of the adjacent detector module 20. However, the embodiments are not limited to these cases. For example, the sensitive portion 21 of the detector module 20 may overlap a portion of the insensitive portion 22 of the adjacent detector module 20.

That is, in the embodiments described above, in the detector modules 20 arranged in the row direction R, when the sensitive portion 21 of one of the adjacent detector modules 20 overlaps at least a portion of the insensitive portion 22 of the other thereof, the insensitive area generated by the insensitive portion 22 included in the detector module 20 can be reduced when compared with a case where the detector modules 20 are arranged without the overlapping portion.

Twelfth Embodiment

In the embodiments described above, the configurations of the X-ray detector 12 and the X-ray CT apparatus 1 have been described. However, the technology disclosed herein can also be implemented as a manufacturing method of the X-ray detector 12 described in the embodiments above.

In that case, for example, the manufacturing method of the X-ray detector 12 includes a step of arranging the detector modules 20 arranged in the row direction R such that, for each pair of the adjacent detector modules 20, the sensitive portion 21 of one of the detector modules 20 overlaps the insensitive portion 22 of the other of the detector modules 20, as described in the embodiments above.

For example, the manufacturing method of the X-ray detector 12 may include a step of arranging the detector modules 20 arranged in the row direction R such that the sensitive portion 21 of each of the detector modules 20 overlaps the top of the insensitive portion 22 of the adjacent detector module 20, as described in the embodiments above.

For example, the manufacturing method of the X-ray detector 12 may include a step of arranging the detector modules 20 in one row in the same direction along the row direction R so as to form one row direction detector module group, as described in the embodiments above.

For example, the manufacturing method of the X-ray detector 12 may include a step of arranging the detector modules 20 arranged in the row direction R at the same tilt angle with respect to the row direction R so that the respective planes of incidence of the X-rays face in the same direction, as described in the first embodiment.

For example, the manufacturing method of the X-ray detector 12 may include a step of arranging the detector modules 20 arranged in the row direction R so as to be individually tilted at different angles with respect to the row direction R so that the respective planes of incidence of the X-rays face the focal point of the X-ray tube 11, as described in the second embodiment.

For example, the manufacturing method of the X-ray detector 12 may include a step of providing a plurality of first shielding plates parallelly arranged with gaps interposed therebetween in the row direction R and a plurality of second shielding plates parallelly arranged with gaps interposed therebetween in the channel direction C orthogonal to the row direction R, and disposing the collimator 121 including, for each pair of the adjacent detector modules 20, the shielding plate 1211 that blocks scattered X-rays incident on a side surface of the sensitive portion 21 of one of the detector modules 20 at a place where the sensitive portion 21 of the one of the detector modules 20 overlaps the insensitive portion 22 of the other of the detector modules 20 along the planes of incidence of the X-rays of the respective detector modules 20 arranged in the row direction R, as described in the third embodiment.

For example, the manufacturing method of the X-ray detector 12 may include a step of providing a plurality of first shielding plates parallelly arranged with gaps interposed therebetween in the row direction R and a plurality of second shielding plates parallelly arranged with gaps interposed therebetween in the channel direction C orthogonal to the row direction R, and arranging the collimators 122, each including, for each pair of the adjacent detector modules 20, a shielding plate 1221 that blocks the scattered X-rays incident on a side surface of the sensitive portion 21 of one of the detector modules 20 at a place where the sensitive portion 21 of one of the detector modules 20 overlaps the insensitive portion 22 of the other of the detector modules 20, individually on the detector modules 20 included in the X-ray detector 12, as described in the fourth embodiment.

For example, the manufacturing method of the X-ray detector 12 may include a step of disposing the collimator 123 including a plurality of shielding plates parallelly arranged with gaps interposed therebetween in the channel direction C orthogonal to the row direction R along the planes of incidence of the X-rays of the respective detector modules 20 arranged in the row direction R, and further providing, on the side surface of each of the detector modules 20, the shielding plate 124 that blocks the scattered X-rays incident on the side surface of the sensitive portion 21 of the detector module 20 at a place where the sensitive portion 21 of the detector module 20 overlaps the insensitive portion 22 of the adjacent detector module 20, as described in the fifth embodiment.

For example, the manufacturing method of the X-ray detector 12 may include a step of providing the reflective materials 2131 tilted along the direction of incidence of the X-rays between a plurality of scintillator elements arranged so as to individually correspond to the respective photodiodes included in the photodiode array 212 on the scintillator 211 included in the sensitive portion 21 of each of the detector modules 20, as described in the sixth embodiment.

For example, the manufacturing method of the X-ray detector 12 may include a step of arranging the detector modules 20 in one of two ranges obtained by dividing one row direction detector module group included in the X-ray detector 12 into two ranges by the row-directional center line ML (refer to FIG. 2) using the method described above, and arranging the detector modules 20 in the other of the ranges so as to be arranged in the same row as that of the detector modules 20 included in the one of the ranges in the opposite direction to the detector modules 20 included in the one of the ranges along the row direction R, and such that the sensitive portion 21 of the detector module 20 included in the one of the ranges and the sensitive portion 21 of the detector module 20 included in the other of the ranges are arranged adjacent to each other at the row-directional center line ML, so as to form one row direction detector module group together with the detector modules 20 included in the one of the ranges, as described in the seventh embodiment.

Thirteenth Embodiment

There are various types of X-ray CT apparatuses, such as rotate/rotate-type (third-generation CT) devices in which the X-ray tube and the detector rotate as a unit around the subject and stationary/rotate-type (fourth-generation CT) devices in which a number of X-ray detection elements are fixed in a ring shape array and only the X-ray tube rotates around the subject, and any one of these types can be applied to the embodiments described above.

Fourteenth Embodiment

In the embodiments described above, the exemplary cases have been described where the technology disclosed herein is applied to the X-ray detector of the X-ray CT apparatus. However, the embodiments are not limited to these cases. For example, the technology disclosed in herein can also be applied equally to the radiation detector of other diagnostic radiology devices, such as an X-ray detector of X-ray diagnostic devices and a gamma radiation detector of PET devices and SPECT devices.

While the embodiments of the radiation detector, the X-ray CT apparatus, and the manufacturing method has been described above, the term "processor" used in the above description refers to, for example, a central processing unit (CPU), a graphics processing unit (GPU), or circuitry such as an application-specific integrated circuit (ASIC), a programmable logic device (such as a simple programmable logic device (SPLD)), a complex programmable logic device (CPLD), or a field-programmable gate array (FPGA). If the processor is, for example, a CPU, the processor reads and executes a computer program stored in a storage circuit to perform the functions. If, instead, the processor is, for example, an ASIC, the functions are directly incorporated into the circuit of the processor as a logic circuit, instead of storing the computer program in the storage circuit. Each processor of the present embodiment is not limited to a case where each processor is configured as a single circuit, but a plurality of independent circuits may be combined into one processor to perform the functions of the processor. Furthermore, a plurality of components in FIG. 1 may be integrated into one processor to perform the functions of the components.

In the embodiments described above, each of the components of each of the devices illustrated in the drawings is functionally conceptual, and need not be physically configured as illustrated. That is, the specific form of dispersion or integration of the devices is not limited to those illustrated in the drawings, and all or some of the devices can be configured in a functionally or physically dispersed or integrated manner in any units according to various types of loads or use conditions. Furthermore, all or any part of the processing functions performed in the devices can be implemented by a CPU and a computer program analyzed and executed by the CPU, or can be implemented as hardware with a wired logic.

Of the processes described in the embodiments above, all or some of the processes described to be automatically performed can also be manually performed, and all or some of the processes described to be manually performed can also be automatically performed using a known method. In addition, the processing procedures, the control procedures, the specific names, and the information including various types of data and parameters illustrated in the above description and the drawings can be freely modified unless otherwise specified.

According to at least one of the embodiments described above, the insensitive area generated by the insensitive portion included in the detector module can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation detector, comprising:

a first detector module comprising, on a surface facing a radiation generation source, a sensitive portion configured to output an analog signal corresponding to incident radiation and an insensitive portion provided with at least a portion of a transmission path of the analog signal output from the sensitive portion; and a second detector module that is a detector module different from the first detector module, comprising, on a surface facing the radiation generation source, a sensitive portion configured to output an analog signal corresponding to the incident radiation and an insensitive portion provided with at least a portion of a transmission path of the analog signal output from the sensitive portion, wherein the sensitive portion of the first detector module is arranged so as to overlap on a surface of the insensitive portion of the second detector module on a side closer to the radiation generation source; and wherein the insensitive portion comprises an analog-to-digital converter configured to convert the analog signal output from the sensitive portion into a digital signal.

2. The radiation detector according to claim 1, wherein the sensitive portion comprises:

a scintillator configured to convert the incident radiation into light; and a photodiode array that is optically connected to the scintillator, and in which a plurality of photodiodes each configured to convert the light into the analog signal are arranged.

3. The radiation detector according to claim 1, wherein the sensitive portion comprises a semiconductor crystal configured to output the analog signal corresponding to energy contained in the incident radiation.

4. The radiation detector according to claim 1, wherein the first detector module and the second detector module are arranged in one row in a same direction along a row direction so as to form one row direction detector module group.

5. The radiation detector according to claim 4, wherein the first detector module and the second detector module are arranged at a same tilt angle with respect to the row direction so that respective planes of incidence of the radiation face in a same direction.

6. The radiation detector according to claim 4, wherein the first detector module and the second detector module are arranged individually at different tilt angles with respect to the row direction so that respective planes of incidence of the radiation face a focal point of the radiation generation source.

7. The radiation detector according to claim 4, further comprising a collimator disposed along respective planes of incidence of the radiation of the first detector module and the second detector module, wherein the collimator comprises a plurality of first shielding plates parallelly arranged in the row direction with gaps interposed between the first shielding plates and a plurality of second shielding plates parallelly arranged in a channel direction orthogonal to the row direction with gaps interposed between the second shielding plates, and the first shielding plates comprise a shielding plate configured to block scattered radiation incident on a side surface of the sensitive portion of the first detector module at a place where the sensitive portion of the first detector module overlaps the insensitive portion of the second detector module.

8. The radiation detector according to claim 4, wherein each of the first detector module and the second detector module individually further comprises a collimator disposed on a plane of incidence of the radiation, the collimator comprises a plurality of first shielding plates parallelly arranged in the row direction with gaps interposed between the first shielding plates and a plurality of second shielding plates parallelly arranged in a channel direction orthogonal to the row direction with gaps interposed between the second shielding plates, and the first shielding plates comprise a shielding plate configured to block scattered radiation incident on a side surface of the sensitive portion of the first detector module at a place where the sensitive portion of the first detector module overlaps the insensitive portion of the second detector module.

9. The radiation detector according to claim 4, further comprising a collimator disposed along respective planes of incidence of the radiation of the first detector module and the second detector module, wherein the collimator comprises a plurality of shielding plates parallelly arranged in a channel direction orthogonal to the row direction with gaps interposed between the shielding plates, and the first detector module further comprises, on a side surface of the module, a shielding plate configured to block scattered radiation incident on a side surface of the sensitive portion of the first detector module at a place where the sensitive portion of the first detector module overlaps the insensitive portion of the second detector module.

10. The radiation detector according to claim 4, wherein the sensitive portion comprises:

a scintillator configured to convert the incident radiation into light; and a photodiode array that is optically connected to the scintillator, and in which a plurality of photodiodes each configured to convert the light into the analog signal are arranged, and the scintillator comprises a plurality of scintillator elements arranged so as to individually correspond to the respective photodiodes, and the scintillator elements are separated from one another by reflective materials tilted along a direction of incidence of the radiation.

11. The radiation detector according to claim 4, further comprising a third detector module and a fourth detector module that have a same structure as that of the first detector module and the second detector module, wherein the third detector module and the fourth detector module are arranged in a same row as that of the first detector module and the second detector module in a direction opposite the first detector module and the second detector module along the row direction so as to form one row direction detector module group together with the first detector module and the second detector module, and the sensitive portion of the second detector module and the sensitive portion of the fourth detector module are arranged so as to be adjacent to each other at a location where a straight line passing through a focal point and an isocenter of the radiation generation source intersects the radiation detector.

12. An X-ray computer tomographic apparatus, comprising:

an X-ray tube; and an X-ray detector, wherein the X-ray detector comprises:

a first detector module comprising, on a surface facing the X-ray tube, a sensitive portion configured to output an analog signal corresponding to incident X-rays and an insensitive portion provided with at least a portion of a transmission path of the analog signal output from the sensitive portion; and a second detector module that is a detector module different from the first detector module, comprising, on a surface facing the X-ray tube, a sensitive portion configured to output an analog signal corresponding to the incident X-rays and an insensitive portion provided with at least a portion of a transmission path of the analog signal output from the sensitive portion, wherein the sensitive portion of the first detector module is arranged so as to overlap on a surface of the insensitive portion of the second detector module on a side closer to the radiation generation source; and wherein the insensitive portion comprises an analog-to-digital converter configured to convert the analog signal output from the sensitive portion into a digital signal.

13. A manufacturing method of a radiation detector that comprises a first detector module comprising, on a surface facing a radiation generation source, a sensitive portion configured to output an analog signal corresponding to incident radiation and an insensitive portion provided with at least a portion of a transmission path of the analog signal output from the sensitive portion, and a second detector module that is a detector module different from the first detector module, comprising, on a surface facing the radiation generation source, a sensitive portion configured to output an analog signal corresponding to the incident radiation and an insensitive portion provided with at least a portion of a transmission path of the analog signal output from the sensitive portion, the manufacturing method comprising arranging the sensitive portion of the first detector module and the insensitive portion of the second detector module so that the sensitive portion of the first detector module is arranged to overlap on a surface of the insensitive portion of the second detector module on a side closer to the radiation generation source;

wherein the insensitive portion comprises an analog-to-digital converter configured to convert the analog signal output from the sensitive portion into a digital signal.

14. A radiation detector, comprising:

a first detector module comprising, on a surface facing a radiation generation source, a sensitive portion configured to output an analog signal corresponding to incident radiation and an insensitive portion provided with at least a portion of a transmission path of the analog signal output from the sensitive portion; and a second detector module that is a detector module different from the first detector module, comprising, on a surface facing the radiation generation source, a sensitive portion configured to output an analog signal corresponding to the incident radiation and an insensitive portion provided with at least a portion of a transmission path of the analog signal output from the sensitive portion, wherein the sensitive portion of the first detector module is arranged so as to overlap on a surface of the insensitive portion of the second detector module on a side closer to the radiation generation source, wherein the first detector module and the second detector module are arranged in one row in a same direction along a row direction so as to form one row direction detector module group, and wherein the first detector module and the second detector module are arranged individually at different tilt angles with respect to the row direction so that respective planes of incidence of the radiation face a focal point of the radiation generation source.

* * * * *